United States Patent [19]
Dan

[11] Patent Number: 5,639,863
[45] Date of Patent: Jun. 17, 1997

[54] HUMAN MONOCLONAL ANTIBODIES SPECIFIC TO CELL CYCLE INDEPENDENT GLIOMA SURFACE ANTIGEN

[76] Inventor: Michael D. Dan, 114 Brookbanks Dr., Don Mills, Ontario, Canada, M3A 2T2

[21] Appl. No.: 264,093

[22] Filed: Jun. 21, 1994

[51] Int. Cl.⁶ .......................... C07K 16/18; C07K 16/30
[52] U.S. Cl. ........................... 530/388.8; 530/388.15; 530/388.2; 530/865; 530/866; 530/350; 530/395; 536/23.53; 536/24.1; 935/15
[58] Field of Search .................. 530/388.15, 388.2, 530/388.8, 865, 866, 350, 395; 536/23.53, 24.1; 935/15

[56] References Cited

FOREIGN PATENT DOCUMENTS 2035088  7/1991  Canada ........................... C12P 21/08

OTHER PUBLICATIONS

Hawkins et al (1992) British Medical Journal 305:1348-1352.
Dan et al (1992) J. Neurosurg. 76:660-669.
Dan et al (1995) 82: 475-480. (Mar. issue).
Roih (1991) "Essential Immunology", Blackwell Scientific Publications, Oxford, pp. 65-68 + 74.

*Primary Examiner*—Toni R. Scheiner
*Attorney, Agent, or Firm*—Ridout & Maybee

[57] ABSTRACT

The variable chains of two human monoclonal antibodies (HMAbs) of the IgM isotype are characterized by elucidation of cDNAs encoding those chains. The HMAbs are specific against cell cycle independent, glioma-associated antigen, and the antibodies do not recognize cultured normal human astrocytes. Immunoconjugates based on the sequences identified should target both proliferating and non-proliferating glioma cells in vivo, thus providing a valuable adjunctive therapy in the treatment of these tumors.

32 Claims, 6 Drawing Sheets

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 363 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:1:

```
CAG GTT CAG CTG GTG CAG TCT GGA GCT GAG GTG AAG AAG CCT GGG GCC       48
TCA GTG AAA GTC TCC TGC AAG GCT TCT GGT TAC ACC TTC ACC ACC TAT       96
GGT CTC AGC TGG GTG CGA CAG GCC CCT GGA CAA GGG CTT GAG TGG ATG      144
GGA TGG ATC AGC GCT CAC AAT GGT AAC ACA AAC TCT GCA CAG AAG TTC      192
CAG GGC AGA GTC TCC ATG ACC ACA GAC ACA TCC ACG AGC ACA GCC TAC      240
ATG GAG GTG AGG AGC CTC AGA TCT GAC GAC ACG GCC GTG TAT TAC TGT      288
GCG CGA GTC GGG GTA TGG GAC CTA TTG AAC TAC TTT GAC TAC TGG GGC      336
CAG GGA ACC CTG GTC ACC GTC TCC TCA                                  363
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:2:

```
TTG GTG GCA GCA GCA ACA GGT GCC CAC TCC                              30
```

( 2 ) INFORMATION FOR SEQ ID NO:3:

( i ) SEQUENCE CHARACTERISTICS:
        ( A ) LENGTH: 121 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:3:

```
Gln Val Gln Leu Val Gln Ser Gly Ala Glu Val Lys Lys Pro Gly Ala
                 5                  10                    15
Ser Val Lys Val Ser Cys Lys Ala Ser Gly Tyr Thr Phe Thr Thr Tyr
            20                  25                  30
Gly Leu Ser Trp Val Arg Gln Ala Pro Gly Gln Gly Leu Glu Trp Met
        35                  40                  45
Gly Trp Ile Ser Ala His Asn Gly Asn Thr Asn Ser Ala Gln Lys Phe
    50                  55                  60
Gln Gly Arg Val Ser Met Thr Thr Asp Thr Ser Thr Ser Thr Ala Tyr
65                  70                  75                  80
Met Glu Val Arg Ser Leu Arg Ser Asp Asp Thr Ala Val Tyr Tyr Cys
                85                  90                  95
Ala Arg Val Gly Val Trp Asp Leu Leu Asn Tyr Phe Asp Tyr Trp Gly
            100                 105                 110
Gln Gly Thr Leu Val Thr Val Ser Ser
            115                 120
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:4:

```
Leu Val Ala Ala Ala Thr Gly Ala His Ser
                 5                  10
```

( 2 ) INFORMATION FOR SEQ ID NO:5:

( i ) SEQUENCE CHARACTERISTICS:
        ( A ) LENGTH: 333 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:5:

```
CAG TCT GTG CTG ACT CAG CCA CCC TCA GCG TCT GGG ACC CCC GGG CAG    48
AGG GTC ACC ATC TCT TGT TCT GGA AGC AGC TCC AAC ATC GGA ACT AAT    96
ACT GTA AAC TGG TAC CTG CAG CTC CCA GGA ACG GCC CCC AAA GTC CTC   144
ATC TAT AGT AAT AAT CAG CGG CCC TCA GGG GTC CCT GAC CGA TTC TCT   192
GGC TCC AAG TCT GGC ACC TCA GCC TCC CTG GCC ATC AGT GGA CTC CAG   240
TCT GAG GAT GAG GCT GAT TAT TTC TGT GCA GCA TGG GAT GAC AGC CTG   288
AAA GGT GTG GTA TTC GGC GGA GGG ACC AAG CTG ACC GTC CTA GGT       333
```

( 2 ) INFORMATION FOR SEQ ID NO:6:

( i ) SEQUENCE CHARACTERISTICS:
        ( A ) LENGTH: 111 amino acids
        ( B ) TYPE: amino acid ( C ) STRANDEDNESS: Not Applicable
( D ) TOPOLOGY: linear ( x i ) SEQUENCE DESCRIPTION: SEQ ID NO:6:

| Gln | Ser | Val | Leu | Thr | Gln | Pro | Pro | Ser | Ala | Ser | Gly | Thr | Pro | Gly | Gln |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Arg | Val | Thr | Ile | Ser | Cys | Ser | Gly | Ser | Ser | Asn | Ile | Gly | Thr | Asn |
|     |     |     | 20  |     |     |     | 25  |     |     |     |     | 30  |     |     |
| Thr | Val | Asn | Trp | Tyr | Leu | Gln | Leu | Pro | Gly | Thr | Ala | Pro | Lys | Val | Leu |
|     |     | 35  |     |     |     |     | 40  |     |     |     |     | 45  |     |     |     |
| Ile | Tyr | Ser | Asn | Asn | Gln | Arg | Pro | Ser | Gly | Val | Pro | Asp | Arg | Phe | Ser |
|     | 50  |     |     |     |     | 55  |     |     |     |     | 60  |     |     |     |     |
| Gly | Ser | Lys | Ser | Gly | Thr | Ser | Ala | Ser | Leu | Ala | Ile | Ser | Gly | Leu | Gln |
| 65  |     |     |     |     | 70  |     |     |     |     | 75  |     |     |     |     | 80  |
| Ser | Glu | Asp | Glu | Ala | Asp | Tyr | Phe | Cys | Ala | Ala | Trp | Asp | Asp | Ser | Leu |
|     |     |     |     | 85  |     |     |     |     | 90  |     |     |     |     | 95  |     |
| Lys | Gly | Val | Val | Phe | Gly | Gly | Gly | Thr | Lys | Leu | Thr | Val | Leu | Gly |
|     |     |     | 100 |     |     |     |     | 105 |     |     |     |     | 110 |     |

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single stranded
( D ) TOPOLOGY: linear ( x i ) SEQUENCE DESCRIPTION: SEQ ID NO:7:

CTC CTC ACT CAC TGT GCA GGG TCC TGG GCC 30

( 2 ) INFORMATION FOR SEQ ID NO:8:

( i ) SEQUENCE CHARACTERISTICS:
( A ) LENGTH: 10 amino acids
( B ) TYPE: amino acid
( C ) STRANDEDNESS: Not Applicable
( D ) TOPOLOGY: linear ( x i ) SEQUENCE DESCRIPTION: SEQ ID NO:8:

| Leu | Leu | Thr | His | Cys | Ala | Gly | Ser | Trp | Ala |
|-----|-----|-----|-----|-----|-----|-----|-----|-----|-----|
|     |     |     |     | 5   |     |     |     |     | 10  |

( 2 ) INFORMATION FOR SEQ ID NO:9:

( i ) SEQUENCE CHARACTERISTICS:
( A ) LENGTH: 339 base pairs
( B ) TYPE: nucleic acid
( C ) STRANDEDNESS: single stranded
( D ) TOPOLOGY: linear ( x i ) SEQUENCE DESCRIPTION: SEQ ID NO:9:

GAT ATT GTG ATG ACC CAG ACT CCA CTC TCC CTG CCC GTC ACC CCT GGA 48
GAG CCG GCC TCC ATC TCC TGC AGG TCT AGT CAG AGC CTC TTG GAT AGT 96
GAT GAT GGA AAC ACC TAT TTG GAC TGG TAC CTG CAG AAG CCA GGG CAG 144
TCT CCA CAG CTC CTG ATC TAT ACG CTT TCC TAT CGG GCC TCT GGA GTC 192
CCA GAC AGG TTC AGT GGC AGT GGG TCA GGC ACT GAT TTC ACA CTG AAA 240
ATC AGC AGG GTG GAG GCT GAG GAT GTT GGA GTT TAT TAC TGC ATG CAA 288
CGT ATA GAG TTT CCT TTC ACT TTC GGC GGA GGG ACC AAG GTG GAG ATC 336
AAA 339

( 2 ) INFORMATION FOR SEQ ID NO:10:

( i ) SEQUENCE CHARACTERISTICS:
        ( A ) LENGTH: 113 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:10:

```
Asp Ile Val Met Thr Gln Thr Pro Leu Ser Leu Pro Val Thr Pro Gly
                 5                  10                  15

Glu Pro Ala Ser Ile Ser Cys Arg Ser Ser Gln Ser Leu Leu Asp Ser
             20                  25                  30

Asp Asp Gly Asn Thr Tyr Leu Asp Trp Tyr Leu Gln Lys Pro Gly Gln
         35                  40                  45

Ser Pro Gln Leu Leu Ile Tyr Thr Leu Ser Tyr Arg Ala Ser Gly Val
     50                  55                  60

Pro Asp Arg Phe Ser Gly Ser Gly Ser Gly Thr Asp Phe Thr Leu Lys
65                   70                  75                  80

Ile Ser Arg Val Glu Ala Glu Asp Val Gly Val Tyr Tyr Cys Met Gln
                 85                  90                  95

Arg Ile Glu Phe Pro Phe Thr Phe Gly Gly Gly Thr Lys Val Glu Ile
                100                 105                 110

Lys
```

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: single stranded
        ( D ) TOPOLOGY: line ( x i ) SEQUENCE DESCRIPTION: SEQ ID NO:11:

```
ATG AGG CTC CCT GCT CAG CTC CTG GGG CTG CTA ATG CTC TGG GTC CCT    48

GGA TCC AGT GAG                                                    60
```

( 2 ) INFORMATION FOR SEQ ID NO:12:

( i ) SEQUENCE CHARACTERISTICS:
        ( A ) LENGTH: 20 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:12:

```
Met Arg Leu Pro Ala Gln Leu Leu Gly Leu Leu Met Leu Trp Val Pro
                 5                  10                  15

Gly Ser Ser Glu
             20
```

( 2 ) INFORMATION FOR SEQ ID NO:13:

( i ) SEQUENCE CHARACTERISTICS:
        ( A ) LENGTH: 360 base pairs
        ( B ) TYPE: nucleic acid
        ( C ) STRANDEDNESS: single stranded
        ( D ) TOPOLOGY: linear ( x i ) SEQUENCE DESCRIPTION: SEQ ID NO:13:

```
GGG GGA GGC TTG GTC CAG CCT GGG GGG TCC CTG AGA CTC TCC TGT TCA    48

GCC TCT GGA TTC ACC TTC AGT AGC TAT GCT ATG CAC TGG GTC CGC CAG    96
```

```
GCT CCA GGG AAG GGA CTG GAA TAT GTT TCG GCT ATT AGT AGT AAT GGG         144

GGT AGC ACA TAC TAC GCA GAC TCC GTG AAG GGC AGA TTC ACC ATC TCC         192

AGA GAC AAT TCC AAG AAC ACT CTG TAT CTT CAA ATG AGC AGT CTG AGA         240

GCT GAG GAC ACG GCT GTG TAT TAC TGT GTG AAA GAC AGG TTA AAA GTG         288

GAG TAC TAT GAT AGT AGT GGT TAT TAC GTT TCT CGG TTC GGT GCT TTT         336

GAT ATC TGG GGC CAA GGG ACA ACG                                         360
```

( 2 ) INFORMATION FOR SEQ ID NO:14:

( i ) SEQUENCE CHARACTERISTICS:
        ( A ) LENGTH: 120 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:14:

```
Gly Gly Gly Leu Val Gln Pro Gly Gly Ser Leu Arg Leu Ser Cys Ser
              5                   10                  15
Ala Ser Gly Phe Thr Phe Ser Ser Tyr Ala Met His Trp Val Arg Gln
            20                  25                  30
Ala Pro Gly Lys Gly Leu Glu Tyr Val Ser Ala Ile Ser Ser Asn Gly
        35                  40                  45
Gly Ser Thr Tyr Tyr Ala Asp Ser Val Lys Gly Arg Phe Thr Ile Ser
    50                  55                  60
Arg Asp Asn Ser Lys Asn Thr Leu Tyr Leu Gln Met Ser Ser Leu Arg
65                  70                  75                  80
Ala Glu Asp Thr Ala Val Tyr Tyr Cys Val Lys Asp Arg Leu Lys Val
                85                  90                  95
Glu Tyr Tyr Asp Ser Ser Gly Tyr Tyr Val Ser Arg Phe Gly Ala Phe
            100                 105                 110
Asp Ile Trp Gly Gln Gly Thr Thr
        115                 120
```

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:15:

```
Thr Tyr Gly Leu Ser
              5
```

( 2 ) INFORMATION FOR SEQ ID NO:16:

( i ) SEQUENCE CHARACTERISTICS:
        ( A ) LENGTH: 17 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:16:

```
Trp Ile Ser Ala His Asn Gly Asn Thr Asn Ser Ala Gln Lys Phe Gln
              5                   10                  15
Gly
```

( 2 ) INFORMATION FOR SEQ ID NO:17:

( i ) SEQUENCE CHARACTERISTICS:
    ( A ) LENGTH: 12 amino acids
    ( B ) TYPE: amino acid
    ( C ) STRANDEDNESS: Not Applicable
    ( D ) TOPOLOGY: linear ( x i ) SEQUENCE DESCRIPTION: SEQ ID NO:17:

Val Gly Val Trp Asp Leu Leu Asn Tyr Phe Asp Tyr
            5                            10

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:18:

Ser Gly Ser Ser Ser Asn Ile Gly Thr Asn Thr Val Asn
            5                        10

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:19:

Ser Asn Asn Gln Arg Pro Ser
            5

( 2 ) INFORMATION FOR SEQ ID NO:20:

( i ) SEQUENCE CHARACTERISTICS:
        ( A ) LENGTH: 11 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:20:

Ala Ala Trp Asp Asp Ser Leu Lys Gly Val Val
            5                      10

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:21:

Ser Tyr Ala Met His
         5

( 2 ) INFORMATION FOR SEQ ID NO:22:

( i ) SEQUENCE CHARACTERISTICS:
        ( A ) LENGTH: 17 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:22:

Ala Ile Ser Ser Asn Gly Gly Ser Thr Tyr Tyr Ala Asp Ser Val Lys
            5                        10                      15

Gly ( 2 ) INFORMATION FOR SEQ ID NO:23:

( i ) SEQUENCE CHARACTERISTICS:
        ( A ) LENGTH: 23 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:23:

Asp Arg Leu Lys Val Glu Tyr Tyr Asp Ser Ser Gly Tyr Tyr Val Ser
            5                        10                  15

Arg Phe Gly Ala Phe Asp Ile
           20

( 2 ) INFORMATION FOR SEQ ID NO:24:

( i ) SEQUENCE CHARACTERISTICS:
        ( A ) LENGTH: 17 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:24:

Arg Ser Ser Gln Ser Leu Leu Asp Ser Asp Asp Gly Asn Thr Tyr Leu
              5                        10                15

Asp ( 2 ) INFORMATION FOR SEQ ID NO:25:

( i ) SEQUENCE CHARACTERISTICS:
        ( A ) LENGTH: 7 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:25:

Thr Leu Ser Tyr Arg Ala Ser
           5

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: Not Applicable
        ( D ) TOPOLOGY: linear ( x i ) SEQUENCE DESCRIPTION: SEQ ID NO:26:

Met Gln Arg Ile Glu Phe Pro Phe Thr
              5

HUMAN MONOCLONAL ANTIBODIES SPECIFIC TO CELL CYCLE INDEPENDENT GLIOMA SURFACE ANTIGEN

The invention relates to the characterization of monoclonal antibodies (MAbs) of the IgM isotype and cDNAs encoding therefor. In particular, the invention relates to two human MAbs against malignant glioma cell lines. These human anti-glioma MAbs are of promising clinical value in the treatment of this aggressive brain tumor. The invention includes the cell surface markers to which these MAbs bind.

Malignant gliomas are the most common of all primary brain tumors. They are also among the most difficult to manage clinically. Depending on their intracranial location, they can grow to a substantial size before causing any symptoms. Their biological behavior is notoriously aggressive, although they rarely metastasize outside of the central nervous system.

Surgery and radiotherapy alone are seldom curative; with the best of care, median survival is under one year. Moreover, despite major efforts to introduce new adjunctive therapies, the prognosis for patients with malignant gliomas has remained essentially unchanged for the past thirty years.

Many adjunctive therapies, including immunotherapy, are either presently ineffective, or carry an unacceptable risk of serious morbidity. With the development of murine hybridomas by Köhler and Milstein (1975); however, tumor immunodiagnosis and immunotherapy with monoclonal antibodies has emerged as a promising area of investigation.

Studies with murine MAbs have already contributed substantially to the understanding of glioma biology and heterogeneity. These reagents are not suited for clinical application in humans for a variety of reasons. In contrast, human MAbs offer the possibilities of greater specificity and biological compatibility than their murine counterparts.

Malignant gliomas are neuroepithelial tumors which commonly arise in the cerebral hemispheres. As a group, they include anaplastic astrocytoma, anaplastic oligodendroglioma, anaplastic ependymona, and glioblastoma multiforme. These tumors all possess certain microscopic features in common such as dense cellularity, increased numbers of mitotic figures, nuclear pleomorphism with hyperchromasis, and cellular pleomorphism. In glioblastoma multiforme, the above features are present, as well as necrosis with pseudopalisades, capillary endothelial proliferation with pseudorosette formation, and mesenchymal proliferation. These tumors are heterogeneous and demonstrate both inter- and intra-tumor variability, which may well be the major determinant of therapeutic resistance. Since few markers exist which are selective for poorly differentiated glioma cells, it would be highly beneficial to selectively target these cells within an otherwise heterogeneous population, as the failure to deplete a tumor of such poorly differentiated cells inevitably results in tumor recurrence.

It is well established that many patients with malignant gliomas are significantly immunosuppressed, especially with regards to cell-mediated functions, although few patients are cachectic. The finding of immunosuppression in the absence of significant systemic wasting would suggest that the former is due to tumor-intrinsic mechanisms, rather than a reflection of excessive tumor burden, as is usually the case. Humoral immune mechanisms in patients with malignant gliomas also appear to be depressed, albeit they remain intact.

Malignant gliomas possess many antigens in common with the normal cells from which they were derived. As a result, it is virtually impossible to prepare conventional heteroantisera to glioma tissue without encountering some degree of cross-reactivity with normal adult brain. The shared antigens may be intracellular, membrane associated, or extracellular in nature.

The role of glycolipids and carbohydrate structures in cellular interaction, differentiation, and oncogenesis has received much attention lately. A subclass of glycolipids known as gangliosides may play an important role in the regulation of cellular adhesion and proliferation. When a cell undergoes malignant transformation, there may be subtle qualitative and quantitative changes in the chemistry of its surface gangliosides.

Malignant gliomas are well vascularized tumors. However, there is a breakdown or total absence of the blood-brain barrier that exists in a normal, healthy brain, in which the brain is normally 'privileged', or isolated from the effects of the immune system or other blood-borne agents. Because of this breakdown of the blood-brain barrier in patients with these tumors, the immune system has access to the tumor cells.

Studies with murine MAbs raised against glioma cell lines were reported by Schnegg, et al. (1981) and Bourdon, et al. (1983). Both groups immunized mice with cultured human glioma cell lines, and fused spleen cells with the mouse myeloma lines P3X63-Ag8 or P3X63-Ag8.653, respectively. The MAbs BF7, GE2, described by Schnegg et al. (1981) appear to be relatively glioma-restricted, whereas antibody CG12 (de Tribolet, et al. 1984) reacts with a spectrum of gliomas, melanomas, and neuroblastomas. Antibody 81C6 was produced and characterized by Bourdon, et al. (1983) and found to react with a glioma-mesenchymal extracellular matrix (GMEM) antigen expressed on gliomas, neuroblastomas, melanomas, sarcomas, and cultured fibroblasts. In addition to the above, the GMEM antigen was also found in normal liver sinusoids, spleen red pulp sinusoids, kidney medullary tubule interstitium, and glomerular mesangium. Whereas absorption of CG12 with normal adult and fetal brain abolished binding activity, neither BF7, GE2, nor 81C6 were affected by the same treatment.

Reports of human monoclonal antibodies (HMAbs) from patients with malignant gliomas have appeared in the literature. However, none of these antibodies have been well characterized.

Sikora, et al. (1982) reported the production of HMAbs reactive to 0.25% glutaraldehyde-fixed glioma cells. These investigators obtained intratumoral lymphocytes from 12 patients undergoing craniotomy for malignant glioma and fused them to the EBNA$^+$ 8-aza-guanine-resistant human lymphoblastoid line LICR-LON-HMy2, which is known to secrete gamma and lambda chains. A total of 71 hybridomas were obtained from 5 patients. No subcloning experiments were reported and no demonstration or proof of the monoclonality of the hybridomas is given. This study also reported cross-reactivity of the HMAbs to other tumor cell lines. The disadvantages of the requirement for intratumoral cells from the human brain as the starting material are clear.

In a subsequent study by Sikora et al. (1983), the authors concluded that, for the HMAb singled out for study, this HMAb was of a low affinity because of the high concentrations necessary to demonstrate reactivity with targets.

The present inventor and coworkers reported the production of five hybridoma cell lines each producing an anti-glioma HMAb of the IgM isotype (Dan, et al. 1992). These five hybridomas were generated by the somatic fusion of peripheral blood lymphocytes from four patients having astrocytic tumors, with a human myeloma-like cell line, TM-H2-SP2.

The production of these five hybridomas was based on the principle that human patients with neurological tumors should possess circulating B lymphocytes with anti-glioma specificities, and based on the principle that tumor-reactive antibodies derived from glioma patients should recognize common, non-allelic determinants in human gliomas which might differ in specificities and distribution from those recognized by xenogeneic systems.

Accordingly, these five hybridomas were derived from fusion of a human myeloma-like line and B cells obtained from human patients suffering from gliomas. By appropriate culturing of the resultant hybridomas, effective HMAbs to human gliomas were obtained in useful quantities.

A remarkable characteristic of the human MAbs obtained is the high degree of similarity amongst them despite being derived from cells obtained from four different tumor patients, each having a different tumor type, history, or stage of tumor development. Also, these HMAbs exhibit increased compatibility with and increased sensitivity for recognition of human target cells as compared to the prior art. The HMAbs do not bind to normal human astrocytes.

These HMAbs are useful in diagnostic imaging for the radiolocalization of neurological tumors, and in immunotherapy by either direct action or by linking these HMAbs to chemotherapeutics which can then be targeted directly to the tumor cells. To be of clinical value, a human MAb should meet the following criteria: 1) label the surface, i.e. bind to, live tumor cells, 2) recognize a cell cycle independent tumor specific antigen, and 3) bind equally well to tumor cells in vitro regardless of their culture viability, growth characteristics, or culture density. Of the five anti-glioma HMAbs obtained, at least two appear to satisfy these criteria and have been characterized. These two HMAbs are designated BT34/A5 and BT32/A6.

The invention provides cDNA sequences coding for the light and heavy chains of the variable regions of the HMAbs BT34/A5 and BT32/A6. The invention includes the corresponding amino acid sequences and human MAbs of the IgM isotype having the characterized variable region chains as well as other proteins or protein conjugates having these chains. In particular, the invention includes any protein or protein conjugate (i.e., immunoconjugate) having variable light and heavy chains with hypervariable regions (complementarity determining regions or CDR) the same as or at least 90% homologous with the hypervariable regions of the light and heavy chains of the invention. As the skilled person will appreciate, immunoconjugates include drugs, toxins, cytokines, radionuclides, enzymes and other diagnostic or therapeutic molecules conjugated to the antigen binding molecular structure. The invention also includes a cell surface marker or antigen to which a HMAb of the invention binds.

Preparation of Human MAbs

Cell fusions were performed, to make hybridomas from the human myeloma-like cell line TM-H2-SP2 and peripheral B lymphocytes (PBL) obtained from eight different brain tumor patients, coded BT-24, BT-27, BT-32, BT-34, BT-38, BT-39, BT-54 and BT-55. These patients, both male and female, ranged from 5 to 55 years of age and had a variety of neuroectodermal tumors including fibrillary astrocytoma, oligoastrocytoma, primitive neuroectodermal tumor, and glioblastoma. The fusions were performed as previously described (Dan, et al. 1992). Incubation of the cells in the 96-microwell trays was conducted using fresh tissue culture media and fetal calf serum (FCS), supplemented with L-glutamine (292 mg/l) and L-asparagine (44 mg/l). The hybridoma outgrowth, defined as the number of microwells containing macroscopic colonies of greater than 50–100 cells (visible to the naked eye) divided by the total number seeded, and expressed as a percentage, ranged from 0–19.5%.

The number of PBL in all samples available for fusion varied from $6.0 \times 10^6$ to $5.8 \times 10^7$. Although the ratio of myeloma cells to lymphocytes remained constant at 1:4 for each fusion, the plating density that was used ranged from $1.0 \times 10^5$ to $2.5 \times 10^5$ myeloma cells per ml of fusion mixture. The lower plating density was chosen in some fusions in attempts to encourage better initial monoclonality, whereas the higher plating density seemed to favor improved hybridoma outgrowth. The concentration of polyethylene glycol was 50% (v/v) in all fusions.

Typically, discernable hybridoma growth appeared from 4 to 6 weeks after a fusion, and new growth in microwells often continued to be observed for several weeks thereafter. In general, those colonies of hybridomas which appeared earliest tended to be the most stable. Not all macroscopic colonies visible at the end of the 96 microwell (0.28 cm$^2$/well) culture period could be successfully propagated to amounts suitable for growth in 24 well dishes (2.01 cm$^2$/well). In fusions with BT-54, for example, of the seven colonies which originally grew in 96 microwells, only one was capable of prolonged growth in vitro. Instances of hybridoma growth failure occurring later than three months post-fusion were not observed.

The hybridomas were screened for the presence of human immunoglobulin and reactivity with 3M KCl extracts of autologous tumors, or glutaraldehyde-fixed glioma cell lines.

A total of 1,121 wells containing growth of putative hybridomas from the fusions described were screened, of which 162 (14.5%) were found to react with tumor extracts, or glioma cell lines. Two of the fusions, namely BT-27 and BT-32, were screened for reactivity with several glioma cell lines, and instances were found of individual microwells which tested positive in multiple ELISAs (enzyme linked immunosorbent assays).

In the last two fusions, BT-54 and BT-55, the ELISA was modified to detect only those microwells which contained reactive IgM species. This modification was accomplished by substituting culture supernatant from hybridoma BT27/2D2 for TM-H2 as a control, and adding alkaline phosphatase conjugated goat anti-human IgM as a second antibody. The reasoning was that analysis of immunoglobulin chains present in 34 hybridomas from fusions BT-24, BT-27, BT-32 and BT-34, indicated that all 34 contained IgM, and a careful study of a few of these hybridomas indicated that the IgM alone was responsible for anti-tumor activity. Hybridoma BT27/2D2, derived from cells of patient BT-27, which was consistently negative in various ELISAs of immune reactivity, was chosen as a non-specific IgM control (1–4 µg/ml).

A total of nine high immunoglobulin-producing hybridomas from the fusion series described were screened for reactivity with the human glioma line SK-MG-1, using the FACS-III Flow Cytometer. Five supernatants derived from the hybridomas, designated as BT27/1A2, BT27/2A3, BT32/A6, BT34/A5 and BT54/B8, were found to label this particular glioma cell line. All five contained tumor-reactive IgM species. Thus, from eight fusions and a total of 59 hybridomas which were macroscopically visible at six weeks, only five (8.4%) reacted with the cell surface of a glioma cell line, and were capable of sustained growth in culture. It was noted that BT27/2A3 labelling of SK-MG-1 is enhanced if the latter is maintained at a high cell density prior to testing.

All five hybridoma supernatants were found to contain μ heavy chains. Only BT34/A5 contained lambda light chains, the other four HMAbs contained kappa light chains. Each HMAb was shown to label the cell surface of human glioma line SK-MG-1 using flow cytometric (FCM) analysis and FITC-conjugated goat anti-human IgM (IgG fraction, μ chain specific; Cappel Laboratories, Cochranville, Pa.), indicating that the IgM molecules were binding to the tumor cell surface membrane (data not shown).

After approximately six months of maintenance in culture, the estimated IgM concentration for BT27/1A2 was 5.0 μg/ml; for BT27/2A3, it was 44 μg/ml, for BT32/A6 3.5 μg/ml, for BT34/A5 2.4 μg/ml, and for BT54/B8 22.4 μg/ml. After a further 6 months in continuous culture, IgM production levels were found to be comparable.

Three of the five HMAbs were tested by ELISA for their relative reactivities. At the initial concentration of supernatant fluid which was tested, the order of reactivity was BT27/2A3>BT27/1A2>BT32/A6, which is the same as the order of their respective IgM concentrations. The final titer, analyzed by ELISA, which gave O.D. readings significantly higher than control IgM baseline was 1:16 for BT27/2A3, 1:4 for BT27/1A2, and 1:2 for BT32/A6. Since this assay involves the addition of an equal volume of PBS, i.e., 50 μl, in the initial step, the initial dilution tested in the ELISA was 1:2. There was no evidence of an initial plateau phase in any of the dilution curves, indicating that under the ELISA conditions which were used, the quantity of tumor extract was not a limiting factor.

Determination of Monoclonality

Genomic DNA was isolated from TM-H2-SP2, BT27/1A2, BT27/2A3, BT32/A6, and BT27/2D2 cells according to Maniatis, et al. (1982). Ten μg of DNA were digested overnight at 37° C. with BamHi and HindIII restriction enzymes (>3 units/μg DNA; Boehinger-Mannheim, West Germany) according to the manufacturer's specified conditions. After digestion, the DNA as subjected to electrophoresis on a 0.8% (w/v) agarose gel (Maniatis, et al. 1982), and transferred to a Genescreen Plus membrane (NEN, Boston, Mass.) by the usual method. Following prehybridization with herring sperm DNA (Boehinger-Mannheim, West Germany), the Southern blot was hybridized (Kaufmann, et al. 1985) overnight at 65° C. with a $^{32}$P-labelled $J_H$ probe (Oncor Inc., Gaithersburg, Md.), specific activity of 5–6× $10^8$/μg. The probe includes the entire human $J_H$ region, and totals 5.6 kbp (Ravetch, et al. 1981). Following washing, the blot was exposed to Kodak X-ray film with intensifying screens at –70° C.

Southern blot analysis revealed that hybridomas BT27/1A2, BT27/2A3, and BT32/A6, each possess two rearranged bands bearing homology to the $J_H$ gene region. Hybridoma BT27/2D2 appeared to possess three such bands. The B cell fusion partner used in these experiments, TM-H2-SP2, had only one band and an apparent deletion. Furthermore, there is no evidence for a TM-H2-SP2 type of rearrangement of the $J_H$ region in any of the "hybridomas". As a control, normal PBL DNA, which is composed of 60–70% T cell derived genetic material, was found to yield a blot profile identical to placental (germline) DNA. There was also a common low MW band containing an unrelated homologous sequence present in each of the samples.

The Ig heavy chain gene is located on chromosome 14 in the human, and is composed of four distinct elements known as $V_H$ (variable), $D_H$ (diversity), $J_H$ (joining), and $C_H$ (constant) regions. In germline DNA these regions are separated by intervening sequences which are spliced out once the cell becomes committed to B cell differentiation.

Originally it was thought that only one chromosome underwent rearrangement while the other remained in the germline configuration (the principle of allelic exclusion). In the mouse heavy chain gene, however, the second chromosome is essentially always rearranged (Nottenburg and Weissman, 1981). It was therefore proposed that for a given cell, the probability of a functional rearrangement had to be very low (Coleclough, et al. 1981). One would thus encounter the situation of two non-functional, or one functional and one non-functional, but very rarely two functional heavy chain rearrangements per cell. These observations are valid for the mouse, and seem to be valid for higher mammalian species as well (Korsmeyer, et al. 1983).

The heavy chain probe used in these experiments spans the entire human germline $J_H$ region. In situations where there has been rearrangement of germline DNA, digestion with the restriction enzymes BamHI and HindIII will produce DNA fragments that differ in length from the 5.6 kbp $J_H$ probe. The finding of two such fragments in each of the hybridoma lanes indicates that two heavy chain rearrangements are detected for each hybridoma which is consistent with a monoclonal origin for each of the three hybridomas.

Flow Cytometry

Flow cytometric analysis of cultured human cell lines and strains was performed with the cells grown to confluence and maintained in that state with exchanges of fresh media at least 24 hrs prior to labelling. Suspension culture cell lines were maintained and used from high cell density cultures, i.e. near saturation. Screening was carried out according to the method outlined above in parallel on two or more separate occasions with established positive cell lines to verify maintenance of immune reactivity of the HMAbs.

Results of FCM screening with human cell lines are summarized in Tables 1 and 2. Several different classes of neuroectodermal, and non-neuroectodermal tumors and tissues were tested. All five HMAbs demonstrated a similar pattern of reactivity for the 30 cell lines which were studied, with few notable exceptions. For example, the human epithelial cervical carcinoma cell line, ME180, reacted with BT27/1A2 and BT27/2A3, but not BT32/A6. Antibodies BT34/A5 and BT54/B8 both failed to react with the glioma cell line SKI-1, but labeled melanoma line M-4.

Only HMAb BT32/A6 had a singular pattern of reactivity. Antibodies BT27/1A2 and BT27/2A3 exhibited one pattern of reactivity, and antibodies BT34/A5 and BT54/B8 had another pattern of reactivity, which differed slightly from each other. None of the HMAbs reacted with any of the hematological cell lines which were tested.

TABLE 1

| | | Reactivity of three HMAbs | | |
|---|---|---|---|---|
| Tumor Type | Cell Line | BT27/1A2[a] | BT27/2A3 | BT32/A6 |
| Glioma | SK-MG-1 | positive[b] | positive | positive |
| | SK-MG-13 | positive | positive | positive |
| | SKI-1 | positive | positive | positive |
| | LM-215 | negative | negative | negative |
| | LM-340 | negative | negative | negative |
| | U-178 | positive | positive | positive |
| | U-373 | positive | positive | positive |
| Melanoma | M-4 | negative | negative | negative |
| | IGR-37 | negative | negative | negative |

TABLE 1-continued

Reactivity of three HMAbs

| Tumor Type | Cell Line | BT27/1A2[a] | BT27/2A3 | BT32/A6 |
|---|---|---|---|---|
| Neuroblastoma | IGR-39 | negative | negative | negative |
|  | IMR-32 | negative | negative | negative |
|  | SK-K-MC | negative | negative | positive |
| Retinablastoma | Y-76 | negative | negative | negative |
| Rematological | CEK-T[c] | negative | negative | negative |
|  | K-562[d] | negative | negative | negative |
|  | HL-60[e] | negative | negative | negative |
| Other Tumors | HeLa[f] | positive | positive | positive |
|  | ME180[f] | positive | positive | negative |
|  | C-33A[f] | negative | negative | negative |
|  | SW1166[g] | negative | negative | negative |
|  | SW1417[g] | negative | negative | negative |
|  | SW948[g] | negative | negative | negative |
|  | HT29[g] | negative | negative | negative |
|  | J82[h] | negative | negative | negative |
| Embryonic | HEF | negative | negative | negative |
| Fibroblast | WI-38 | negative | negative | negative |

Footnotes:
[a]hybridomas,
[b]cells were detected to have bound HMAb above the background level of labelling with control antibody,
[c]T-cell leukemia,
[d]chronic myelocytic leukemia,
[e]acute promyelocytic leukemia,
[f]epithelial cervical carcinoma,
[g]colonic adenocarcinoma,
[h]transitional bladder cell carcinoma,
N.D.: not done.

TABLE 2

Reactivity of HMAbs BT34/A5 and BT54/B8

| Tumor Type | Cell Line | BT34/A5[a] | BT54/B8 | BT27/2A3 |
|---|---|---|---|---|
| Glioma | SK-MG-1 | positive[b] | positive | positive |
|  | SKI-1 | negative | negative | positive |
|  | U-373 | positive | positive | positive |
| Melanoma | M-4 | positive | positive | negative |
| Hematological | CCRF-CEM[a] | negative | negative | negative |
|  | K-562[d] | negative | negative | negative |
|  | HL-60[e] | negative | negative | negative |
|  | U-937[f] | negative | negative | N.D. |
|  | Raji[g] | negative | negative | N.D. |
| Other Tumors | HeLa[h] | negative | negative | positive |
|  | ME180[h] | negative | negative | negative |
|  | C-33A[h] | negative | negative | negative |
|  | SW1417[i] | negative | negative | negative |
|  | SW1463[i] | negative | negative | negative |
|  | J82[j] | negative | negative | negative |
| Embryonic | IMR-90 | positive | positive | N.D. |
| Fibroblast | WI-38 | negative | negative | negative |

Footnotes:
[a]hybridomas,
[b]see TABLE 1,
[c]T-cell leukemia,
[d]chronic myelocytic leukemia,
[e]acute promyelocytic leukemia,
[f]histiocytic lymphoma, monocyte-like,
[g]B cell lymphoma,
[h]epithelial cervical carcinoma,
[i]colonic adenocarcinoma,
[j]transitional bladder cell carcinoma,
N.D.: not done.

Despite some minor differences in the pattern of reactivity against a panel of human tumor cell lines, all five HMAbs appear to be recognizing similar molecular substances, both in terms of biochemical composition and biological distribution even though being derived from four different patients with different tumors.

Immunoperoxidase Staining

The antibody BT32/A6 was chosen for an immunoperoxidase staining assay using a panel of tumor cells. Tumor cells were grown on coverslips for 2–3 days in complete medium, washed with PBS and fixed with 2% formaldehyde for 20 minutes at room temp. After being washed with PBS, cells were incubated with 1% normal goat serum for 60 minutes. After another wash with PBS, cells were incubated with either 10–20 µg/mL MAb or control human myeloma IgM for 120 minutes at room temp. After another wash with PBS, cells were stained with biotinylated goat anti-human IgM for 60 minutes at room temp, then incubated with HRP labeled streptavidin for another 60 minutes, followed by washing with PBS. The peroxidase reaction was initiated using 0.06% diaminobenzidine with 0.01% hydrogen peroxide in 50 mM Tris-HCl buffer, pH 7.0, for 10 minutes. The cells were briefly counterstained with hematoxylin. As shown in Table 3, the staining results largely confirm the flow cytometry results with the exceptions being positive binding of HMAb to melanoma and neuroblastoma cell lines using this assay.

TABLE 3

Reactivity of HMAb BT32/A6-Peroxidase Staining

| Tumor Type | Cell Line | BT32/A6 |
|---|---|---|
| Glioma | SK-MG-1 | positive |
|  | U-373 | positive |
|  | U-118 | positive |
|  | U-87 MG | positive |
| Neuroblastoma | SK-N-SH | positive |
|  | SK-N-MC | positive |
| Melanoma | SK-MEL 5 | positive |
|  | SK-MEL 3 | positive |
|  | SK-MEL 28 | positive |
|  | A-375 | positive |
| Breast | BT-20 | positive |
| Carcinoma | MDA MB-468 | positive |
|  | MCF-7 | positive |
| Colon | HT-29 | negative |
| Carcinoma | SK-CO1 | negative |
| Human | WI-38 | negative |
| Fibroblast | MRC-5 | negative |

Reactivity with Normal Human Astrocytes

Cultured human astrocytes were assessed for labelling with HMAbs. All reagents were checked for immune reactivity against an established positive human glioma cell line (U-373). None of the HMAbs BT27/1A2, BT27/2A3, and BT32/A6 appeared to label cultured astrocytes from two different individuals. Antibodies BT34/A5 and BT54/B8 also failed to label normal human astrocytes obtained from one individual.

Relative Affinity

To determine relative antibody affinities of the five HMAbs, a modification of the method of De Bernado and Davies (1987) was used. The results of ELISAs of the five HMAbs with tumor extract from patient BT-37 (glioblastoma multiforme) after either a long (18 hr) or a short (4 hr) incubation at 4° C., were expressed in terms of O.D. measurements. Comparison of the O.D. reading for each HMAb at the two time points indicates that there is a statistically significant (p<0.05) increase in O.D. for BT32/A6 and BT54/B8 with the longer incubation. None of the other 3 HMAbs (BT27/1A2, BT27/2A3, and BT34/A5) showed a significant increase in reactivity after a longer incubation at 4° C. These observations would suggest that BT32/A6 and BT54/B8 behave as a low affinity antibodies at low temperatures.

After the long incubation period (18 hrs at 4° C.), all five HMAbs confirmed positive (p<0.05) by ELISA when compared to the control. After the short incubation time (4 hrs at 4° C.), however, only BT27/1A2, BT27/2A3, and BT34/A5 were significantly positive; BT32/A6 and BT54/B8 did not react significantly, possibly because of their low affinity nature.

Preliminary Antigen Characterization

Dot blots of total lipid extracts from cultured neuroectodermal cell lines were examined. LN-340 and M-4 are glioma and melanoma cell lines which have been previously shown to be unreactive with any of the five HMAbs. Compared to control HMAb BT27/2D2, there was some indication of potential reactivity for all five HMAbs when tested against glycolipids from the glioma cell line U-373. As for the glioma line SK-MG-1, all the HMAbs except for BT54/B8 seemed to exhibit some degree of reactivity to the lipid extract, although the quality of these dot blots was not entirely satisfactory.

Immunochromatography of total lipid extract prepared from SK-MG-1 glioma cells was performed using BT34/A5 and the parental line, TM-H2, as control. A single specific band with Rf=0.60 was observed. As well, a non-specific band with Rf=0.80 was evident in both the BT34/A5 and TM-H2 lanes. In separate experiments, similar results were obtained for BT27/1A2 and BT27/2A3 compared to BT27/2D2, i.e. a specific band at Rf=0.60. Immunochromatography with HMAb BT54/B8 failed to reveal the presence of any specific banding pattern, but this result is consistent with the dot blot experiment.

These results suggest that the HMAbs recognize a determinant of a glycolipid, or ganglioside, which was not detected in association with glycoproteins.

Human Monoclonal Antibody BT32/A6

HMAb BT32/A6 was selected for further characterization.

Cell culture supernatants of BT32/A6 were prepared by growing the cells in RPMI-1640 medium, supplemented with 10% fetal bovine serum (FBS), 1% L-glutamine and 1% HT (Gibco, Grand Island, N.Y.) either in T175 sq. cm. flasks (Costar, Cambridge, Mass.), or 3 L stir flasks (Kontes, Vineland, N.J.). After four or five days of growth, at a cell density 1–2×10$^6$ per ml, the supernatants were harvested by centrifugation for 10 min. at 500 g. This supernatant was either used directly or concentrated and purified before use. For the concentration of cell culture supernatants, 100,000 molecular weight cut-off tangential flow membranes were used in a minitan concentrator (Millipore, Bradford, Mass.). The purification of IgM antibody was carried out in column chromatography involving mixed mode ion exchange ABx (J. T. Baker Inc., Phillipsburg, N.J.), Q-Sepharose Fast Flow and Superose-6 (Pharmacia, Uppsala, Sweden). The final concentration of MAb was determined in antigen capture ELISA using standard curve generated with polyclonal human IgM (Cappel Labs., Malvern, Pa.).

As reported (Dan, et al. 1992), FCM analysis of SK-MG-1 glioma cells (originally designated AJ; Pfreundschuh, et al. 1978) revealed the presence of two distinct cell populations, designated as "small" and "large" cells (based on forward scatter profiles). This observation was based on work with SK-MG-1 glioma cells that had been removed from tissue culture flasks by mechanically scraping the cells from the flask. When SK-MG-1 cells are removed with trypsin or EDTA, which are less harsh on the cells, FCM analysis demonstrates only one cell population (results not shown). Fluorescence activated sorting of scraped SK-MG-1 cells revealed that the "small" cells had a 2.0% colony-forming efficiency (CFE), whereas the "large" cells were found to have a CFE of 38.0%, almost 20 times greater. When scraped SK-MG-1 glioma cells were labeled with PI (propidium iodide) alone, an increase in PI fluorescence was observed only among the "small" cells, but not among the "large" cells. Since dead cells will stain with PI, it was concluded that the "large" cells of scraped SK-MG-1 are viable and the "small" cells non-viable.

Surface Labeling of Live Cells

Figure 1A:
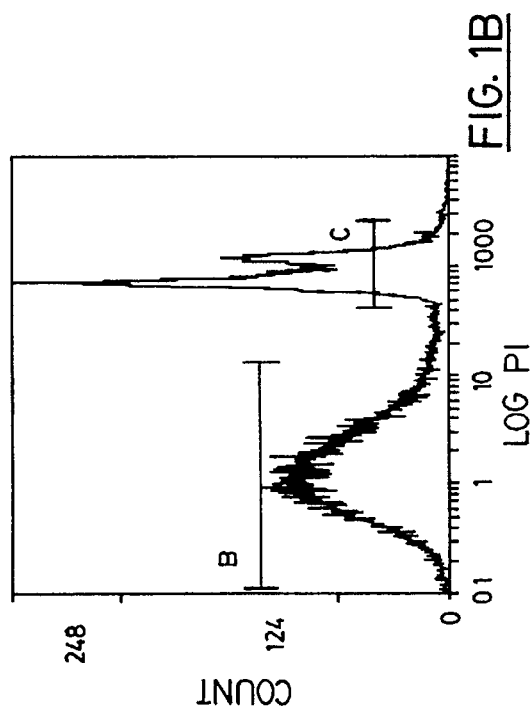
FIGS. 1A–1D are flow cytometric analyses of scraped SK-MG-1 cells.
Figure 1B:
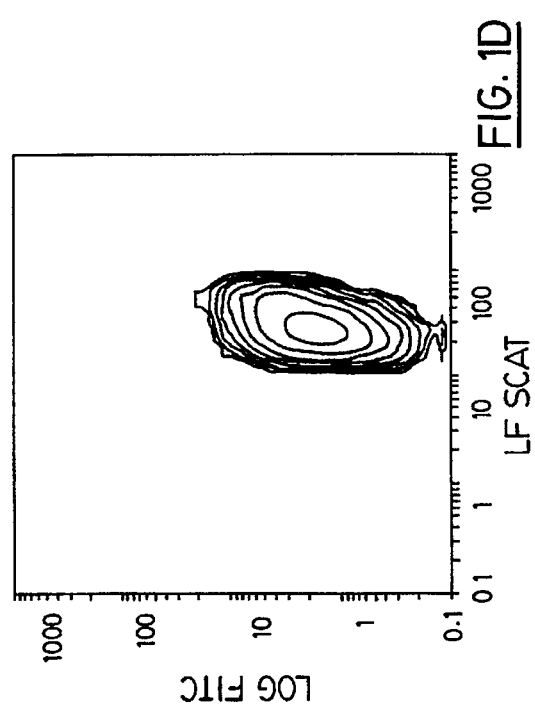
Figure 1C:
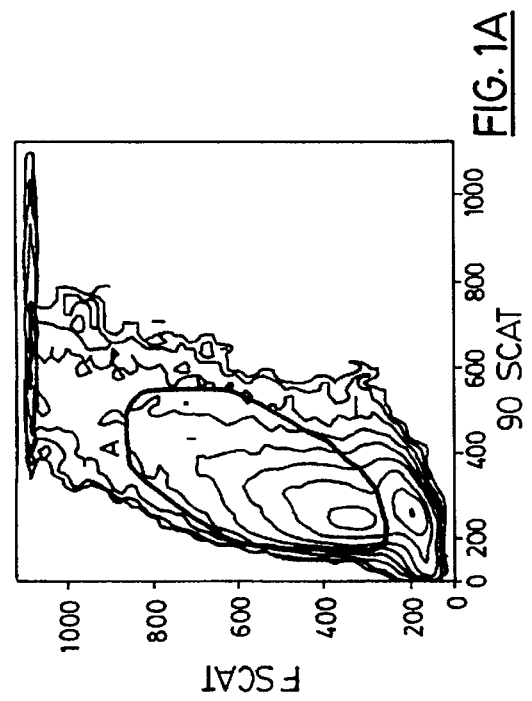
Figure 1D:
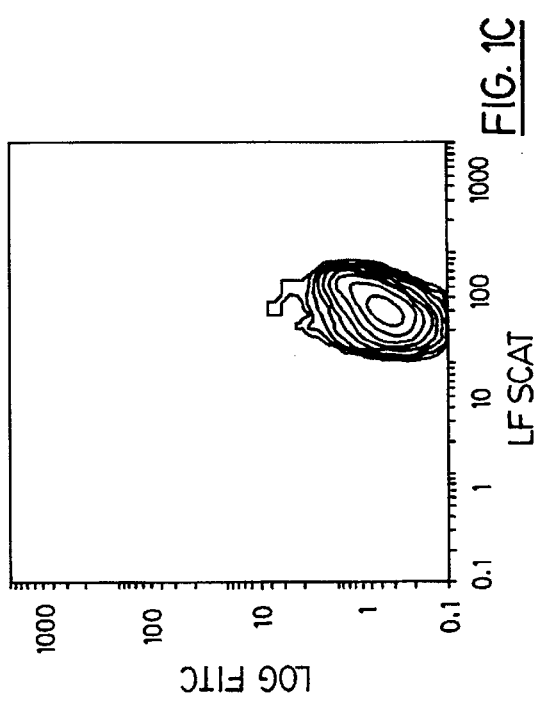

When the non-viable "small" cells are backgated onto the forward scatter v. 90° scatter profile, they appear as a separate population below the viable "large" cells on the ordinate. An area was defined around the "large" cells (region 'A' in FIG. 1A, and PI was added to all FCM specimens to further assist with the task of gating on only live and viable SK-MG-1 glioma cells. In FIG. 1B, a region marked 'B' denotes the SK-MG-1 cells that were unlabeled by PI. The double peak to the right of 'B' represents SK-MG-1 glioma cells which have taken up PI (region 'C'), and are thus non-viable. The double peak corresponds to the $G_0/G_1$ and $G_2/M$ peaks of the cell cycle, respectively. FIG. 1C represents SK-MG-1 cells which were double-gated from region 'A' and region 'B', and are therefore live and capable of forming colonies in vitro. These cells have been labeled with control MAb. The mean FITC fluorescence of these cells was found to increase by a factor of >360% after addition of HMAb BT32/A6 (FIG. 1D). The human IgM MAb BT32/A6, therefore, labels the surface of live SK-MG-1 glioma cells that are viable and capable of forming colonies in vitro.

Cell Cycle Independent Antigen Expression

Figure 2A:
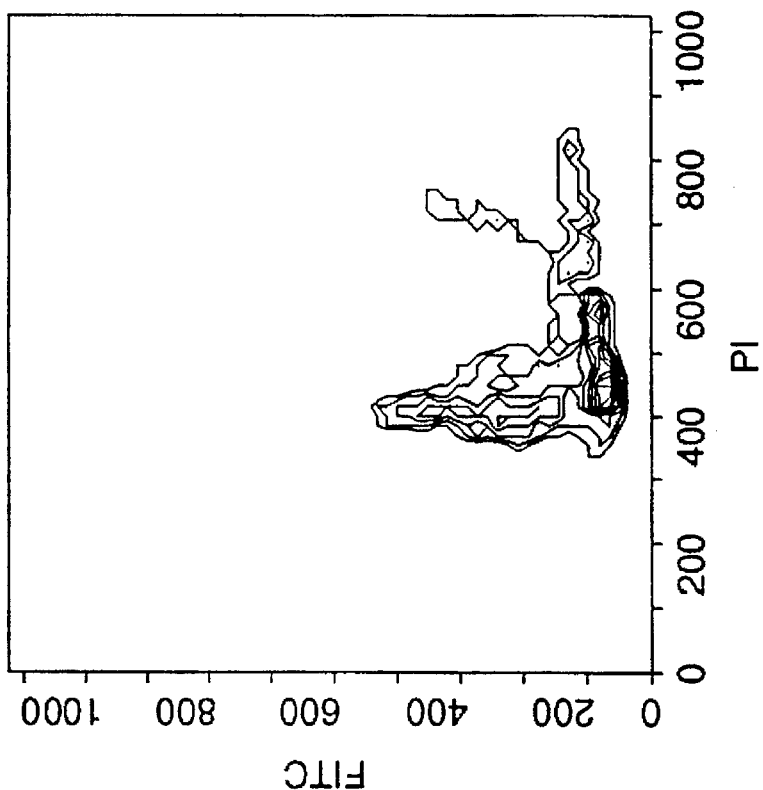
FIGS. 2A and 2B are flow cytometric analyses of glioma cells permeable to PI labeled with BT32/A6 (FIG. 2B) vs. a control (FIG. 2A).
Figure 2B:
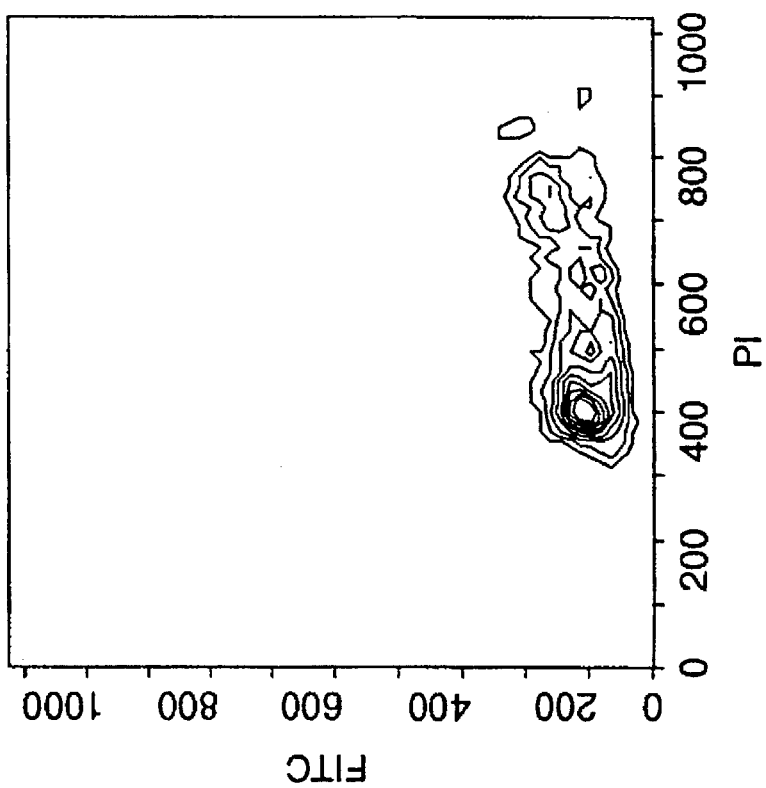

The expression of the BT32/A6 antigen throughout the cell cycle was studied by gating on SK-MG-1 glioma cells that were permeable to PI (FIG. 1B, Region 'C') and labeled with MAb BT32/A6. The results, shown in FIG. 2B, indicate labeling of tumor cells in both the $G_0/G_1$ and $G_2/M$ phases of the cell cycle. There was minimal labeling of SK-MG-1 cells in the S phase of the cell cycle, which is not reflected in the figure.

The observation of labeling throughout each phase of the cell cycle is supported by the finding of increased fluorescence in nearly 100% of viable SK-MG-1 cells. At any time a certain proportion of the SK-MG-1 cells will be in each phase of the cell cycle. The fact that nearly 100% of the cells were labeled must mean that all SK-MG-1 cells in each phase of the cell cycle were labeled by MAb BT32/A6. Thus, the expression of BT32/A6 antigen on the surface of live cells is unaffected by the cell cycle state at the cell passage ratio and culture density of SK-MG-1 which was studied.

Antigen Expression and Culture Split Ratio

Figure 3:
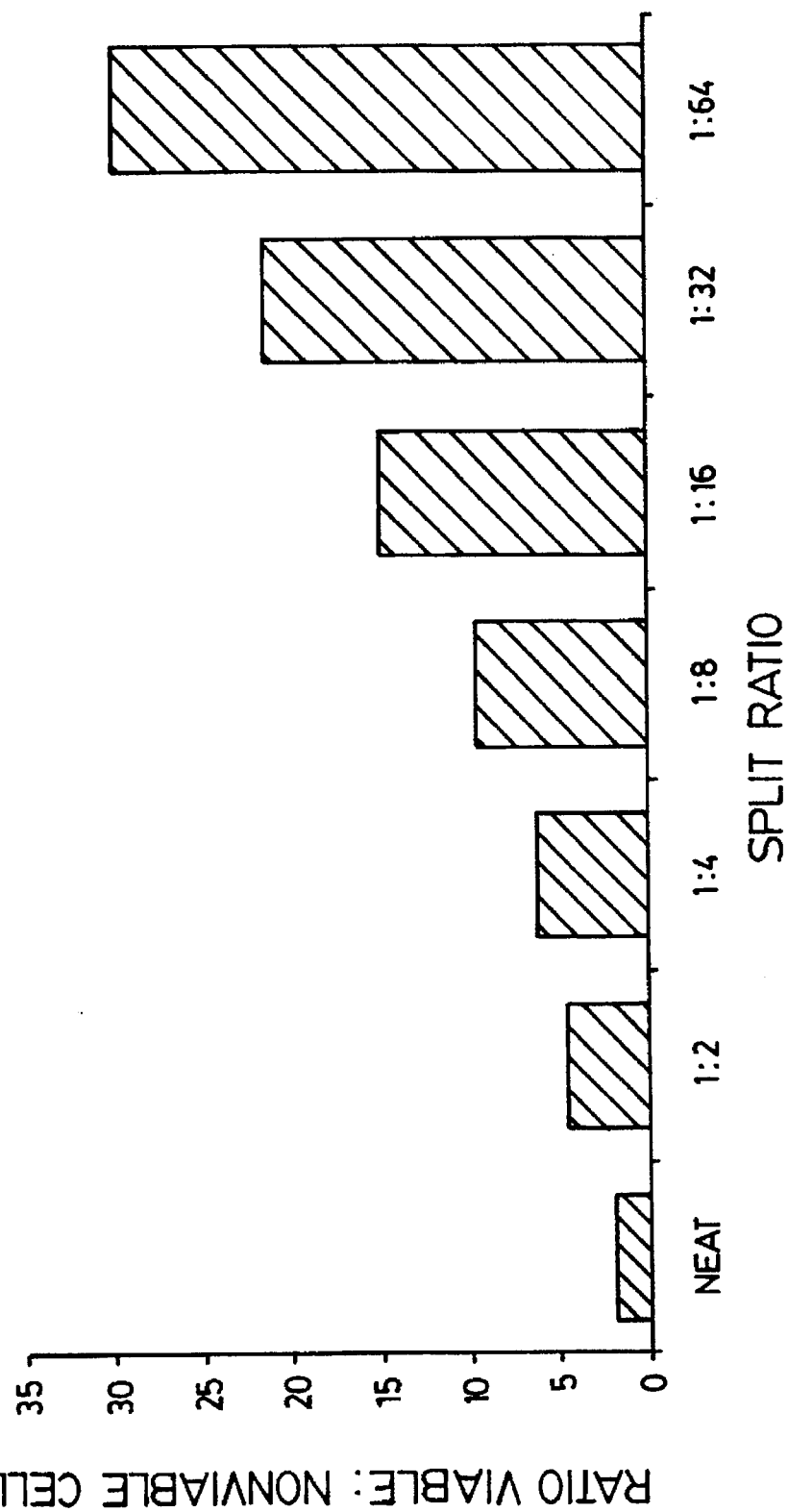
FIG. 3 shows ratios of viable to non-viable cells by passaging confluent cultures of SK-MG-1 cells at various split ratios.
Figure 4:
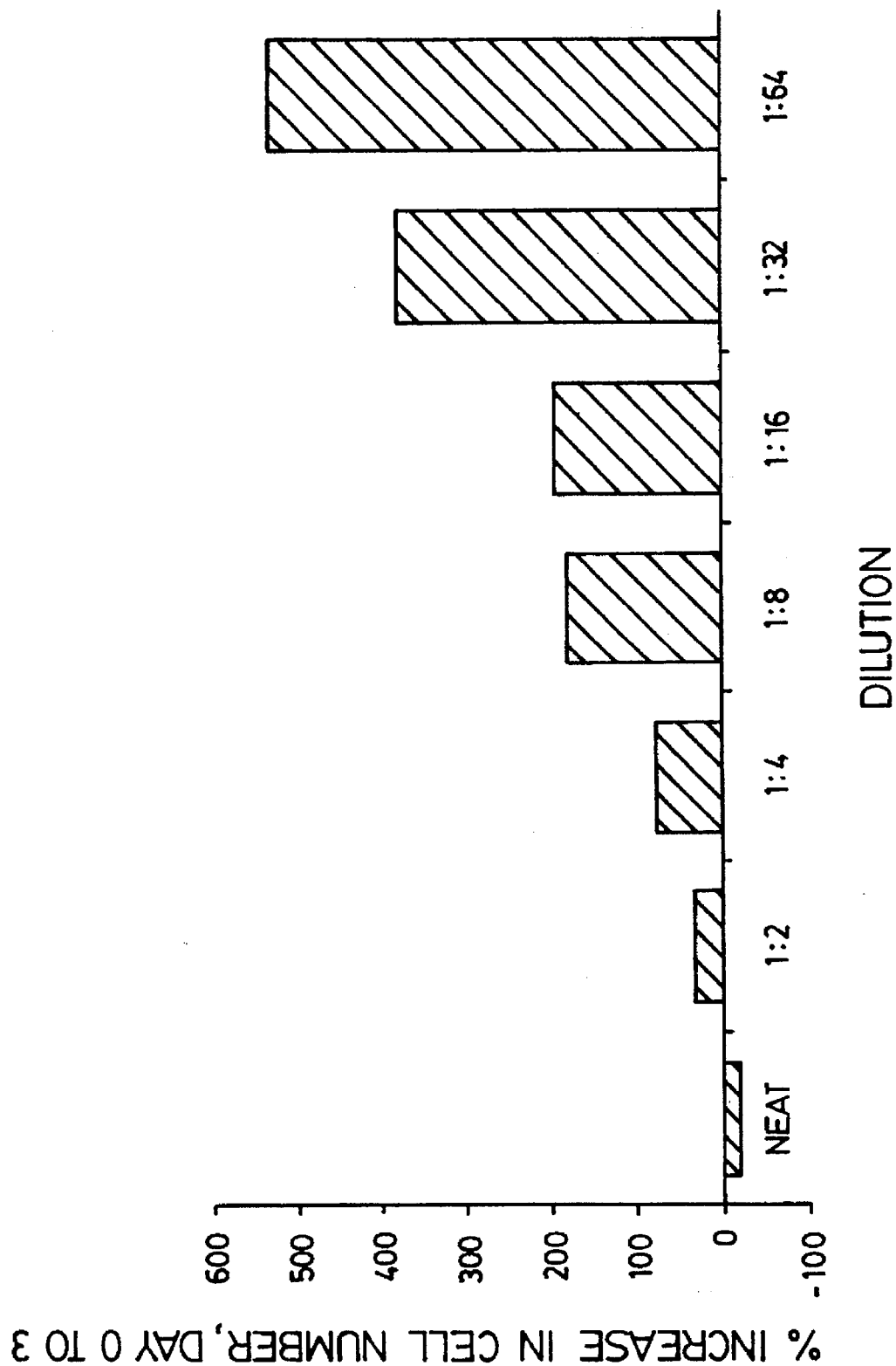
FIG. 4 shows cell growth rates of the various split ratios.
Figure 5:
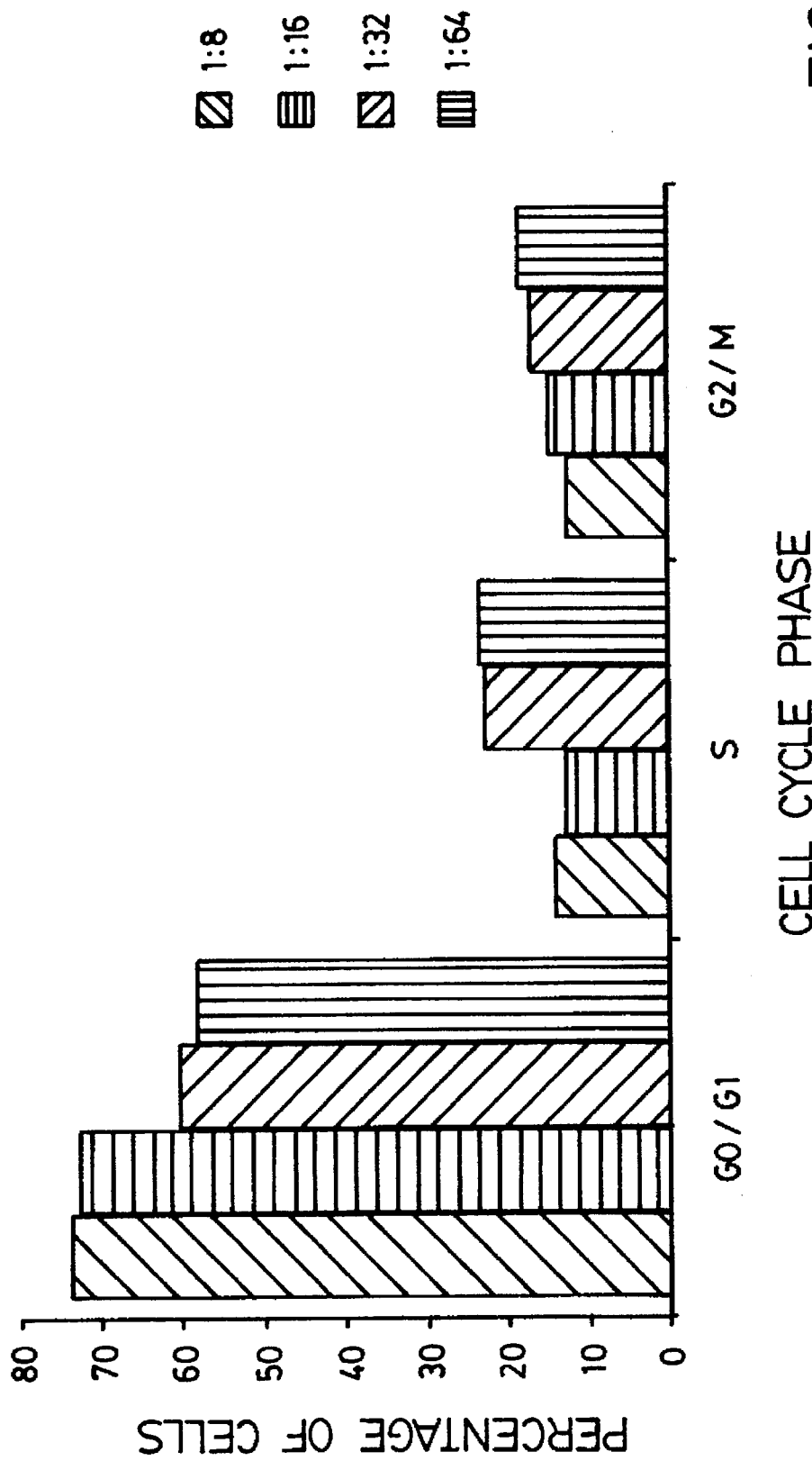
FIG. 5 shows the relative numbers of cells in each phase of the cell cycle for the various split ratios. The trends shown agree with the increase in growth rate shown in FIG. 4.

By passaging confluent cultures of SK-MG-1 glioma cells at split ratios of 0, 1:2, 1:4, 1:8, 1:16, 1:32, and 1:64, then growing the cells under standard conditions for 3 days, significant trends were produced in the following parameters: 1) the ratio of viable to non-viable cells (FIG. 3), 2) cell growth rate (FIG. 4), 3) and the relative number of cells in $G_0/G_1$, S, and $G_2/M$ phases of the cell cycle (FIG. 5). There was an excellent correlation between culture viability (determined by the ratio of viable to non-viable cells) and cell growth rate (determined by cell number on day 3 expressed as a percentage of cell number on day 0) with r=0.991, and p<0.01.

Figure 6:
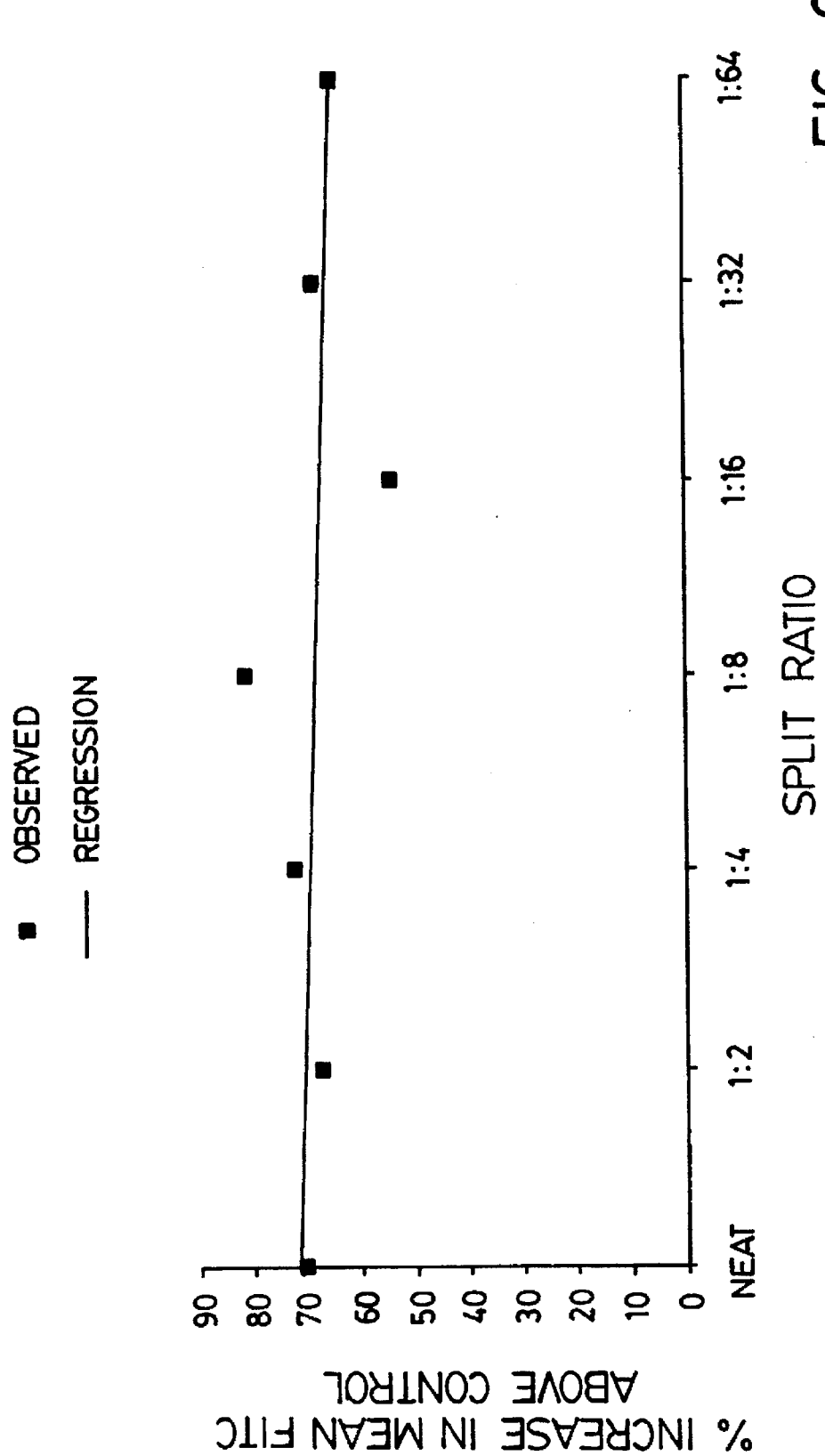
FIG. 6 shows labeling of SK-MG-1 cells by MAb BT32/A6 vs. culture split ratio.

Against these trends in culture viability, growth rate, and cell cycle stage, no significant trend in MAb BT32/A6 labeling of SK-MG-1 glioma cells as a function of culture split ratio was observed (r=-0.303, p>0.05, FIG. 6). The data failed to reject the null hypothesis that the slope of the regression line was zero using Student's t-test. Thus, the MAb BT32/A6 labeling of SK-MG-1 is independent of: 1) culture viability, 2) growth rate, and 3) cell cycle state across the range of passage split ratios which were studied.

Complement Mediated Cytotoxicity

Human glioma (SK-MG-1) cells were washed with RPMI-1640 medium containing 5% FBS and 5 mM HEPES, pH 7.2. Fifty µl of SK-MG-1 cell suspension, with 5×10⁵ cell/ml, were incubated in round bottom microtiter wells of a 96-well plate (Costar, Cambridge, Mass.) with 50 µl of either medium (control) or different dilutions of MAb (test sample) for 2 hours at room temp. All samples were run in duplicate. The microtiter plate was then centrifuged for 5 min. at 400 g, the supernatant was removed and 50 µl of either culture medium or 1:10 dilution of rabbit complement (Cederlane Laboratories, Hornby, ON, Canada) was added in to each well. Incubation was continued for 90 min. at 37° C. After the incubation, the plate was centrifuged for 5 min. at 400 g, 25 µl of supernatant was removed and placed on ice. At the end of the analysis, a sample of cell suspension was stained with an equal volume of 0.2% trypan blue, and the percentage of viable cells was enumerated in a hemocytometer. The mean viabilities of duplicate samples were calculated. The percentage of specific cytotoxicity due to MAb was determined according to the formula:

$$\% \text{ cytotoxicity} = \frac{\% \text{ of viable cells in } C \text{ control} - \% \text{ of viable cells in test sample}}{\% \text{ of viable cells in } C \text{ control}}$$

The results are summarized in Table 4.

TABLE 4

Complement Dependent Cytotoxicity of Human MAb BT32/A6

| Cell Lines | | Percentage of Cytotoxicity Concentration of HMAb (µg/ml) | | |
|---|---|---|---|---|
| | | 20 | 10 | 5 |
| Glioblastoma | | | | |
| SK-MG-1 | + MAb + C[a] | 42 | 38 | 38 |
| | + C | 4 | 4 | 4 |
| U 118 | + MAb + C | ND[b] | 55 | 33 |
| | + C | ND | 14 | 14 |
| Neuroblastoma | | | | |
| SK-S-NH | + MAb + C | 23 | 20 | 18 |
| | + C | 17 | 17 | 7 |
| Normal Human Cells | | | | |
| PBL | + MAb + C | 8 | 7 | 7 |
| | + C | 6 | 6 | 6 |

Footnotes:
[a]rabbit complement,
[b]not done.

Characterization of HMAbs BT32/A6 and BT34/A5

DNA sequences were obtained for the variable regions of the light and heavy chains of HMAbs BT32/A6 and BT34/A5 using standard procedures (Le Boeuf et al. (1989), Schroeder et al. (1990)). Thus, mRNA was extracted from hybridoma cell lines BT32/A6 and BT34/A5 and V-region cDNA was amplified using PCR with primers specific for V-region sequences. Suitable cloning expression vectors were prepared and bacterial cultures were grown in LB medium containing ampicillin. Minipreps of dsDNAs were prepared by the ALKALI method (Molecular Cloning, Maniatis) and DNA was sequenced using the United States Biochemical kit and protocol.

As the DNA sequences of the light and heavy chain constant regions of human IgMs are known, the sequencing of the variable regions of a human IgM results in full characterization.

The various sequences are presented in the Sequence Listing. The HMAb BT34/A5 has a cDNA coding sequence for the $V_{H(\mu)}$ chain of 363 nucleotides (SEQ ID NO:1). A partial signal sequence for $V_{H(\mu)}$ BT34/A5 of 30 nucleotides (SEQ IQ NO:2) was also elucidated. These cDNA coding sequences indicate that BT34/A5 $V_{H(\mu)}$ consists of 121 amino acid residues (SEQ ID NO:3), and the partial signal sequence consists of 10 amino acid residues (SEQ ID NO:4).

The $V_{L(\lambda)}$ chain of HMAb BT34/A5 has a cDNA coding sequence of 333 nucleotides (SEQ ID NO:5), coding for a protein chain of 111 amino acid residues (SEQ ID NO:6). A partial signal sequence of 30 nucleotides (SEQ ID NO:7) coding for 10 amino acid residues (SEQ ID NO:8) was also elucidated.

The HMAb BT32/A6 $V_{L(\kappa)}$ chain has a cDNA coding sequence of 339 nucleotides (SEQ ID NO:9) coding for a protein chain of 113 amino acid residues (SEQ ID NO:10). A signal sequence of 60 nucleotides (SEQ ID NO:11) coding for 20 amino acid residues (SEQ ID NO:12) was elucidated.

The sequences for the $V_{H(\mu)}$ chain of the HMAb BT32/A6 were not completely elucidated, with only partial sequencing in the FR1 and FR4 regions. Thus, the partial cDNA coding sequence for this $V_{H(\mu)}$ chain is 360 nucleotides (SEQ ID NO:13) coding for a protein chain of 120 amino acid residues (SEQ ID NO:14).

Initial analysis of these sequence results indicates, at least for $V_{H(\mu)}$ of BT32/A6, that the antigen binding site is likely in the CDR3 region, i.e., amino acids 92–114 of SEQ ID NO:14.

The hypervariable or complementarity determining regions (CDRs) of the V chains characterized herein are of particular interest as at least some of them are involved in binding antigen. Thus, the invention includes those molecules having immunoglobulin light and heavy variable chains with CDRs being at least 90% homologous with those CDRs characterized herein.

Thus, the $V_{H(\mu)}$ chain of HMAb BT34/A5 has the following complementarity determining regions (CDR):

| | |
|---|---|
| CDR 1 | SEQ ID NO:15 |
| CDR 2 | SEQ ID NO:16 |
| CDR 3 | SEQ ID NO:17 |

The $V_{L(\lambda)}$ chain of HMAb BT34/A5 has the following CDRs:

| | |
|---|---|
| CDR 1 | SEQ ID NO:18 |
| CDR 2 | SEQ ID NO:19 |
| CDR 3 | SEQ ID NO:20 |

The $V_{H(\mu)}$ chain of HMAb BT32/A6 has the following CDRs:

| | |
|---|---|
| CDR 1 | SEQ ID NO:21 |
| CDR 2 | SEQ ID NO:22 |
| CDR 3 | SEQ ID NO:23 |

The $V_{L(\kappa)}$ chain of HMAb BT32/A6 has the following CDRs:

| | |
|---|---|
| CDR 1 | SEQ ID NO:24 |
| CDR 2 | SEQ ID NO:25 |
| CDR 3 | SEQ ID NO:26 |

Discussion

The data present herein show that the expression of the antigen recognized by MAb BT32/A6 is exceptional in that it appears that virtually 100% of SK-MG-1 cells (as determined by FCM) express this antigen regardless of their culture density, culture viability, or cell cycle state. Due to the similarity of HMAb BT34/A5 to BT32/A6, a similar result would be expected for BT34/A5 binding. The reason this antigen recognition is so remarkable is that malignant gliomas are usually thought of as heterogeneous tumors, and it is exceptional to find a common biological thread among all cells in a given tumor. Indeed, heterogeneity is a common feature of most if not all neoplastic tissues; it may arise through 'normal' mechanisms, or result from an increased genetic instability which is intrinsic to the cancer cell. It has been suggested that in the strictest sense, the term 'tumor heterogeneity' should be reserved for situations in which there are differences in cell lineage. Cell cycle effects and other epigenetic phenomena add another level of complexity to the picture of tumor cell variability.

Few tumor-specific MAbs exist that recognize 100% of all neoplastic cells, even in a highly passaged line such as SK-MG-1. In an excellent study utilizing computer-assisted cytofluorometry, Stavrou, et al. 1989, reported on two such MAbs, MUC 8-22 and MUC 2-63, which recognize up to 100% of certain cultured astrocytoma and glioblastoma lines (e.g. 86HG-63, 86HG-39), although such observations were rare. The same group of authors found that the percentage of cells which showed antibody binding varied from one cell line to another and even within individual cell lines at different passage levels.

A human MAb (CLN-IgG) that recognizes a glioma-associated antigen whose surface expression is influenced by cell cycle state has been reported by Kokunai, et al. 1990. Expression of the antigen recognized by CLN-IgG was shown to be markedly increased on the surface of glioma cells in the $G_2/M$ phase of the cell cycle, but significantly reduced on cells in the $G_0/G_1$ phase. These findings have important therapeutic implications, since most conventional adjuvant therapies (e.g. radiotherapy, chemotherapy) are directed towards cycling tumor cells, and it is among the more mitotically quiescent, non-cycling cell populations that the tumor stem cells are thought to reside. If MAb-based tumor immunotherapy is to succeed, it must target tumor cells that are mitotically quiescent as well as those that are actively dividing. This requirement means that the MAb must be directed to lineage-dependent rather than cell-cycle dependent tumor-associated antigens.

So far, there has only been one other report of a MAb directed to an astrocytoma-associated antigen which is expressed in a cell-cycle independent fashion (Sarawar et al. 1991), as demonstrated by FCM analysis. This particular MAb, designated M2, is a murine MAb that recognizes antigenic determinants expressed on a wide variety of central nervous system tumors, including: juvenile astrocytomas, ependymomas, medulloblastomas, meningiomas, and oligodendrogliomas. M2 was also found to react with astrocytes in all areas of normal human adult brain, as well as with a small number of neurons, and with fetal brain.

The human MAb, BT32/A6, therefore, recognizes a cell cycle independent, glioma-associated antigen which is expressed on 100% of viable SK-MG-1 cells, but not on cultured normal human astrocytes. Expression of the BT32/A6 antigen is unaffected by cell density, growth rate, or culture viability. This characteristic makes MAb BT32/A6, and by analogy other HMAbs similarly obtained, well suited for adjunctive immunotherapy in the treatment of human malignant gliomas. By constructing immunotoxins based on the variable region sequences of MAb BT32/A6, it should be possible to target both proliferating (S, $G_2/M$) as well as non-proliferating ($G_0/G_1$) glioma cells in vivo.

REFERENCES

Bourdon, M. A., C. J. Wikstrand, H. Futhmayr, T. J. Matthews, and D. D. Bigner (1983). Human glioma-mesenchymal extracellular matrix antigen defined by monoclonal antibody. Cancer Research 43:2796–2805.

Coleclough, C., R. P. Perry, K. Karjalainen, and M. Weigert (1981). Aberrant rearrangements contribute significantly to the allelic exclusion of immunoglobulin gene expression. Nature 290:372–375.

Dan M D, Schlachta C M, Guy J, et al (1992): Human antiglioma monoclonal antibodies from patients with astrocytic tumors, J. Neurosurg 76:660–669.

De Barnardo, E., and T. F. Davies (1987). A study of human-human hybridomas from patients with autoimmune thyroid disease. J. Clin. Immunol. 7:71–77.

De Tribolet, N., S. Carrel, J. P. Mach (1984). Brain tumor-associated antigens. Prog. Exp. Tumor Res. 27:118–131.

Kaufmann, G., M. Zannis-Hadjopoulos, and R. G. Martin (1985). Cloning of nascent monkey DNA synthesized early in the cell cycle. Mol. Cell. Biol. 5:721–727.

Köhler, G., and C. Milstein (1975). Continuous cultures of fused cells secreting antibody of predefined specificity. Nature 256:495–497.

Kokunai T., Tamaki N., Matsumoto S (1990): Antigen related to cell proliferation in malignant gliomas recognized by a human monoclonal antibody, J. Neurosurg 73:901–908.

Korsmeyer, S. J., A. Arnold, A. Bakhshi, J. V. Ravetch, U. Siebenlist, P. A. Hieter, S. O. Sharrow, T. W. LeBien, J. H. Kersey, D. G. Poplack, P. Leder, and T. A. Waldmann (1983). Immunoglobulin gene rearrangement and cell surface antigen expression in acute lymphocytic leukemias of T cell and B cell precursor origins. J. Clin. Invest. 71:301–313.

Le Boeuf, R. D., F. S. Galin, S. K. Hollinger, S. C. Peiper, and J. E. Blalock (1989). Cloning and sequencing of immunoglobulin variable-region genes using degenerate oligodeoxyribonucleotides, Gene 82:371–77.

Maniatis, T., E. F. Fritsch, and J. Sambrook (1982). Molecular Cloning: A Laboratory Manual, New York, Cold Spring Harbor Laboratories.

Nottenburg, C., and I. L. Weissman (1981). Cμ gene rearrangement of mouse immunoglobulin genes in normal B cells occurs on both the expressed and nonexpressed chromosomes. Proc. Natl. Acad. Sci. U.S.A. 78:484–488.

Pfreundschuh M., Shiku H., Takahashi T, et al (1978): Serological analysis of cell surface antigens of malignant human brain tumors, Proc Natl Acad Sci USA 75:5122–5126.

Ravetch, J. V., U. Siebenlist, S. Korsmeyer, T. Waldmann, and P. Leder (1981). Structure of the human immunoglobulin μ locus: characterization of embryonic and rearranged J and D genes. Cell 27:583–591.

Sarawar S. R., Bonshek R. E., Marsden H. B., et al (1991): A monoclonal antibody which discriminates between subtypes of astrocytoma, Anticancer Res 11:1429–1432.

Schnegg, J. F., A. C. Diserens, S. Carrel, R. S. Accola, and N. de Tribolet (1981). Human glioma-associated antigens detected by monoclonal antibodies. Cancer Res. 41:1209–1213.

Schroeder, H. W. and Wang, J. Y. (1990): Preferential utilization of conserved immunoglobulin heavy chain variable gene segments during human fetal life, Proc. Natl. Acad. Sci. USA 87:6146–50.

Sikora, K., T. Alderson, and J. Phillips (1982). Human hybridomas from malignant gliomas. Lancet i:11–14.

Sikora, K., T. Alderson, J. Ellis, J. Phillips, and J. Watson (1983). Human hybridomas from patients with malignant disease. Br. J. Cancer 47:135–145.

Stavrou D., Bise K., Groeneveld J., et al (1989): Antigenic heterogeneity of human brain tumors defined by monoclonal antibodies, Anticancer Res 9:1489–1496.

I claim:

1. An isolated DNA coding for the variable region of the heavy chain, subgroup μ, ($V_{H(\mu)}$) of the human monoclonal antibody BT34/A5 having the nucleotide sequence SEQ ID NO:1.

2. An isolated DNA as claimed in claim 1, further comprising a nucleotide signal sequence extending from the 5' end of said DNA, the signal sequence comprising at its 3' end the nucleotide sequence SEQ ID NO:2.

3. An isolated DNA coding for the variable region of the light chain, subgroup λ, ($V_{L(\lambda)}$) of the human monoclonal antibody BT34/A5 having the nucleotide sequence SEQ ID NO:5.

4. An isolated DNA as claimed in claim 3, further comprising a nucleotide signal sequence extending from the 5' end of said DNA, the signal sequence comprising at its 3' end the nucleotide sequence SEQ ID NO:7.

5. An isolated DNA coding for the variable region of the heavy chain, subgroup μ, ($V_{H(\mu)}$) of the human monoclonal antibody BT32/A6 comprising the nucleotide sequence SEQ ID NO:13.

6. An isolated DNA coding for the variable region of the light chain, subgroup κ, ($V_{L(\kappa)}$) of the human monoclonal antibody BT32/A6 having the nucleotide sequence SEQ ID NO:9.

7. An isolated DNA as claimed in claim 6, further comprising a nucleotide signal sequence extending from the 5' end of said DNA, the signal sequence having the nucleotide sequence SEQ ID NO:11.

8. The immunoglobulin $V_{H(\mu)}$ chain having the amino acid sequence SEQ ID NO: 3.

9. The $V_{H(\mu)}$ chain as claimed in claim 8, further comprising a signal sequence having the amino acid sequence SEQ ID NO:4 at its C-terminal end.

10. An immunoglobulin which binds the glioma-associated cell surface antigen bound by HMAb BT34/A5, said immunoglobulin $V_{H(\mu)}$ chain having complementarity-determining regions (CDRs) with the amino acid sequences SEQ ID NO:15 (CDR1), SEQ ID NO:16 (CDR2) and SEQ ID NO:17 (CDR3) or sequences being at least 90% homologous therewith.

11. The immunoglobulin $V_{L(\lambda)}$ chain having the amino acid sequence SEQ ID NO:6.

12. The $V_{L(\lambda)}$ chain as claimed in claim 11, further comprising a signal sequence having the amino acid sequence SEQ ID NO:8 at its C-terminal end.

13. An immunoglobulin which binds the glioma-associated cell surface antigen bound by HMAb BT34/A5, said immunoglobulin $V_{L(\lambda)}$ chain having CDRs with the amino acid sequences SEQ ID NO:18 (CDR 1), SEQ ID NO:19 (CDR2) and SEQ ID NO:20 (CDR 3) or sequences being at least 90% homologous therewith.

14. An immunoglobulin having $V_{H(\mu)}$ and $V_{L(\lambda)}$ chains having the amino acid sequences SEQ ID NO:3 and SEQ ID NO:6 respectively.

15. An immunoglobulin as claimed in claim 14 which is a monoclonal antibody.

16. An immunoglobulin as claimed in claim 15 of the isotype M.

17. The human monoclonal antibody BT34/A5.

18. An immunoconjugate which binds the glioma-associated cell surface antigen bound by HMAb BT34/A5, said immunoconjugate having $V_{H(\mu)}$ chains with CDRs having the amino acid sequences SEQ ID NO:15 (CDR1), SEQ ID NO:16 (CDR2) and SEQ ID NO:17 (CDR3) or sequences being at least 90% homologous therewith, and said immunoconjugate having $V_{L(\lambda)}$ chains with CDRs having the amino acid sequences SEQ ID NO:18 (CDR1), SEQ ID NO:19 (CDR2) and SEQ ID NO:20 (CDR3) or sequences being at least 90% homologous therewith.

19. An immunoglobulin conjugate as claimed in claim 18, which is an immunotoxin.

20. The immunoglobulin $V_{H(\mu)}$ chain having the amino acid sequence SEQ ID NO:14.

21. An immunoglobulin which binds the glioma-associated cell surface antigen bound by HMAb BT32/A6, said immunoglobulin $V_{H(\mu)}$ chain having CDRs with the amino acid sequences SEQ ID NO:21 (CDR1), SEQ ID NO:22 (CDR2) and SEQ ID NO:23 (CDR3) or sequences being at least 90% homologous therewith.

22. The immunoglobulin $V_{L(\kappa)}$ chain having the amino acid sequence SEQ ID NO:10.

23. The $V_{L(\kappa)}$ chain as claimed in claim 22, further comprising a signal sequence having the amino acid sequence SEQ ID NO:12.

24. An immunoglobulin which binds the glioma-associated cell surface antigen bound by HMAb BT32/A6, said immunoglobulin $V_{L(\kappa)}$ chain having CDRs with the amino acid sequences SEQ ID NO:24 (CDR1), SEQ ID NO:25 (CDR2) and SEQ ID NO:26 (CDR3) or sequences being at least 90% homologous therewith.

25. An immunoglobulin having $V_{H(\mu)}$ and $V_{L(\kappa)}$ chains having the amino acid sequences SEQ ID NO:14 and SEQ ID NO:10 respectively.

26. An immunoglobulin as claimed in claim 25 which is a monoclonal antibody.

27. An immunoglobulin as claimed in claim 26 of the isotype M.

28. The human monoclonal antibody BT32/A6.

29. An immunoconjugate which binds the glioma-associated cell surface antigen bound by HMAb BT32/A6, said immunoconjugate having $V_{H(\mu)}$ chains with CDRs having amino acid sequences SEQ ID NO:21 (CDR1), SEQ ID NO:22 (CDR2) and SEQ ID NO:23 (CDR3) or sequences being at least 90% homologous therewith, and said immunoconjugate having $V_{L(\kappa)}$ chains with CDRs having the amino acid sequences SEQ ID NO:24 (CDR1), SEQ ID NO:25 (CDR2) and SEQ ID NO:26 (CDR3) or sequences being at least 90% homologous therewith.

30. An immunoconjugate as claimed in claim 29, which is an immunotoxin.

31. An isolated glioma-associated cell surface antigen which is specifically bound by HMAb BT32/A6 and which antigen is not present on the surfaces of normal human astrocytes, said antigen being expressed during each cell cycle stage.

32. An isolated glioma-associated cell surface antigen which is specifically bound by HMAb BT34/A5 and which antigen is not present on the surfaces of normal human astrocytes, said antigen being expressed during each cell cycle stage.

* * * * *